(12) United States Patent
Lawrence et al.

(10) Patent No.: US 8,047,819 B2
(45) Date of Patent: Nov. 1, 2011

(54) TUBING HOLDING DEVICE FOR ROLLER PUMPS

(75) Inventors: Robert J. Lawrence, Brooklyn Park, MN (US); Walt L. Carpenter, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1118 days.

(21) Appl. No.: 11/526,150

(22) Filed: Sep. 22, 2006

(65) Prior Publication Data

US 2008/0213113 A1 Sep. 4, 2008

Related U.S. Application Data

(60) Provisional application No. 60/720,013, filed on Sep. 23, 2005.

(51) Int. Cl.
*F04B 43/08* (2006.01)
*F04B 43/12* (2006.01)
(52) U.S. Cl. .................. 417/477.1; 417/476; 417/477.2
(58) Field of Classification Search .................. 417/476, 417/477.1, 477.2; 248/68.1
See application file for complete search history.

(56) References Cited

U.S. PATENT DOCUMENTS

| 1,834,404 | A | * | 12/1931 | Koch | 248/68.1 |
|---|---|---|---|---|---|
| 5,060,810 | A | * | 10/1991 | Jones | 211/59.4 |
| 5,533,877 | A | * | 7/1996 | Friedmann et al. | 417/477.1 |
| 5,820,048 | A | * | 10/1998 | Shereyk et al. | 248/68.1 |
| 6,561,471 | B1 | * | 5/2003 | Hawie | 248/201 |
| 2004/0141863 | A1 | | 7/2004 | Harada et al. | |
| 2007/0073097 | A1 | | 3/2007 | Borra et al. | |

FOREIGN PATENT DOCUMENTS

| EP | 1 400 691 | 9/2003 |
|---|---|---|
| GB | 1 366 995 | 9/1974 |
| WO | WO 2005/088130 | 9/2005 |

* cited by examiner

*Primary Examiner* — Devon C Kramer
*Assistant Examiner* — Peter J Bertheaud

(57) ABSTRACT

A tubing holding device for a roller pump is disclosed. The tubing holding device is removable from the roller pump, slidably moveable and able to be opened to allow for easy exchange of tubing in roller pumps. The tubing holding device comprises a clamping mechanism that securely holds tubing in place. Tubing of various sizes may be used within a roller pump by selecting the appropriately sized tubing holding device, or by using a tubing holding device, such as one embodiment disclosed, which may be adjustable for different sizes of tubing. Roller pumps including the tubing holding devices, and methods of loading such roller pumps are also disclosed.

17 Claims, 16 Drawing Sheets

TUBING HOLDING DEVICE FOR ROLLER PUMPS

CROSS REFERENCE TO RELATED APPLICATION

This application claims the benefit of U.S. Provisional Application having Ser. No. 60/720,013, filed Sep. 23, 2005, entitled "TUBING HOLDING DEVICE FOR ROLLER PUMPS," which application is incorporated herein by reference in its entirety.

FIELD OF THE INVENTION

The present invention relates to roller pumps used in medical devices or systems (e.g., heart-lung bypass machines). More particularly, the present invention relates to a tubing holding device for roller pumps that is moveable and able to be opened to allow for easy exchange of tubing in roller pumps.

BACKGROUND OF THE INVENTION

Roller pumps have many uses in the medical field. For example, roller pumps are used as blood pumps during hemodialysis or cardiopulmonary bypass. Generally, medical roller pumps consist of a pump head and a pump drive, with the pump head comprising a pump stator and a pump rotor. The pump stator is essentially a hollow chamber having a surface against which one or more hoses or tubing are compressed by the pump rotor. The pump rotor, which is rotatable about its longitudinal axis, is arranged in the pump stator in such a manner that the pump rotor engages tubing positioned in the pump stator with two or more rollers. On rotation of the pump rotor, the rollers compress the tubing as they are rolled along the tubing. A fluid medium contained in the tubing is then transported in a direction of the pump rotor rotation. In order to deter the tubing from wandering within the pump stator while under the influence of the rollers, one or more ends of tubing sections entering and exiting the pump stator are typically fastened in place relative to the pump stator. For roller pumps with reversible running direction, it is usual to provide a fastening at both ends of the tubing within the pump stator.

In some roller pumps, fastening means for holding tubing in place in a pump stator are inserts that latch together to hold the tubing and are screwed into place on the pump stator. The inserts come in many different sizes, each for one size of tubing. The disadvantage of using such fastening inserts is that they need to be screwed out and back in for each necessary tubing size change, which is not efficient.

Another tubing fastening arrangement for a roller pump is described in U.S. Pat. No. 5,533,877. The described fastening arrangement is a detachable piece from a pump head that includes two individual fasteners for attaching two sections of tubing. The detachable piece, including both individual fasteners, has grooves that are slid on proturbances on the pump head to allow for detachment and reattachment of the whole detachable piece. In order to change the tubing in the detachable piece, the detachable piece must be completely removed from the pump head.

Thus, it is desirable to have a tubing holding device for a roller pump that enables easy exchange of tubing configurations in the roller pump.

SUMMARY OF THE INVENTION

The present invention overcomes the shortcomings of the prior art with respect to tubing holding devices for roller pumps by providing tubing holding devices that are easily removable from roller pumps, allowing for easy exchange of tubing holding devices of different tubing sizes. Additionally, the tubing holding devices can be partially removed and opened so that the devices do not have to be completely removed from the roller pump in order to exchange tubing of the same size. Another advantage of the tubing holding devices is that during tubing loading in a vertically oriented roller pump, the preferred configuration of the tubing lumen in the tubing holding device maintains the tubing in place in an open lumen prior to the tubing holding device being closed around the tubing. Also, the tubing holding devices can hold more than one piece of tubing at a time when necessary. Further, some embodiments of the tubing holding devices of the present invention are adjustable to accommodate different sizes of tubing, therefore not requiring complete removal of the device from the roller pump to make tubing size changes.

A first aspect of the present invention is a tubing holding device. One embodiment of the first aspect is a tubing holding device used in a pump comprising a rigid walled cavity, the tubing holding device comprising: a first arm; and a second arm, wherein the first and second arms each define a portion of a lumen that is used to fixedly capture tubing, wherein at least one of the first and second arms is moveable relative to the other arm to allow the lumen to be opened to load tubing into or remove tubing from the lumen, or closed to fixedly capture tubing in the lumen, wherein the first and second arms are sized and shaped and have an outer surface to allow the tubing holding device to be slid into the rigid walled cavity of the pump causing the tubing holding device to be maintained in a closed position when in the rigid walled cavity of the pump. The lumen of the tubing holding device may comprise an outer surface, and the lumen outer surface of the first arm may be greater than the lumen outer surface of the second arm. The tubing holding device may further comprise a means for pivoting at least one of the first and second arms relative to the other arm. The lumen of the tubing holding device may be adjusted in size. The tubing holding device may further comprise at least one shim, wherein the at least one shim is positioned in the lumen to permit the lumen to fixedly capture tubing of a different size. The first and second arms of the tubing holding device may define portions of a plurality of lumens.

A second embodiment of the first aspect is a tubing holding device comprising: a first arm; and a second arm, wherein the first and second arms each define a portion of a lumen that is used to fixedly capture tubing, wherein at least one of the first and second arms is moveable relative to the other arm to allow the lumen to be opened to load tubing into or remove tubing from the lumen, or closed to fixedly capture tubing in the lumen, wherein the lumen comprises an outer surface, and wherein the lumen outer surface of the first arm is greater than the lumen outer surface of the second arm.

A second aspect of the present invention is a roller pump for pumping fluids through a tubing comprising: a pump stator comprising a hollow chamber having a surface, and at least a portion of at least one rigid walled cavity; a pump rotor comprising at least one roller and having a longitudinal axis, wherein the pump rotor is arranged in the hollow chamber of the pump stator for rotation about its longitudinal axis, and wherein when tubing is positioned in the roller pump, a first portion of the tubing is positioned against the surface of the pump stator, and during rotational movement of the pump rotor, the first portion of tubing is compressed against the surface of the pump stator by the at least one roller of the pump stator as the at least one roller travel along the first portion of tubing; and at least one tubing holding device that comprises a first arm and a second arm, wherein the first and second arms each define a portion of a lumen that is used to fixedly capture a second portion of tubing relative to the pump stator, wherein at least one of the first and second arms is moveable relative to the other arm to allow the lumen to be opened to load the second portion of tubing into or remove the second portion of tubing from the lumen, or closed to fixedly capture the second portion of tubing in the lumen relative to the pump stator, wherein the at least one tubing holding device is slidingly disposed in the at least one rigid walled cavity, and wherein when the at least one tubing holding device is slid into the rigid walled cavity to a fully engaged position, the tubing holding device is maintained in a closed position. When the at least one tubing holding device is slid to a partially engaged position in the at least one rigid walled cavity of the roller pump, the lumen may be opened. The roller pump may further comprise a front plate that is removably attached to the pump stator, wherein the at least one rigid walled cavity further comprises at least a portion of the front plate. The at least one tubing holding device may be disengageable from the roller pump and may be exchanged with a different tubing holding device.

A third aspect of the present invention is a method of loading a tubing in a roller pump, wherein the roller pump comprises a pump stator that comprises at least a portion of at least one rigid walled cavity, a pump rotor, and at least one tubing holding device that comprises a first arm and a second arm, the first and second arms each define a portion of a lumen, wherein at least one of the first and second arms is moveable relative to the other arm, and the at least one tubing holding device is slidingly disposed in the at least one rigid walled cavity. One embodiment of the method comprises the steps of: moving the at least one tubing holding device to a partially engaged position in the rigid walled cavity; moving the first arm of the at least one tubing holding device relative to the second arm to open the lumen; placing a portion of the tubing in the lumen of the at least one tubing holding device; moving the first arm of the at least one tubing holding device relative to the second arm to close the lumen and fixedly capture the portion of tubing; and sliding the at least one tubing holding device into the rigid walled cavity so as to fixedly position the portion of tubing relative to the pump stator. The lumen may comprise an outer surface, and the lumen outer surface of the second arm may be greater than the lumen outer surface of the first arm, and in which case, in the placing step, the portion of tubing is placed in the portion of the lumen that is adjacent to the lumen outer surface of the second arm.

DETAILED DESCRIPTION OF THE INVENTION

With reference to the accompanying figures, wherein like components are labeled with like numerals throughout the several figures, tubing holding devices for roller pumps, roller pump designs including tubing holding devices, and methods of loading tubing in roller pumps are disclosed, taught and suggested by the multiple embodiments.

Figure 1:
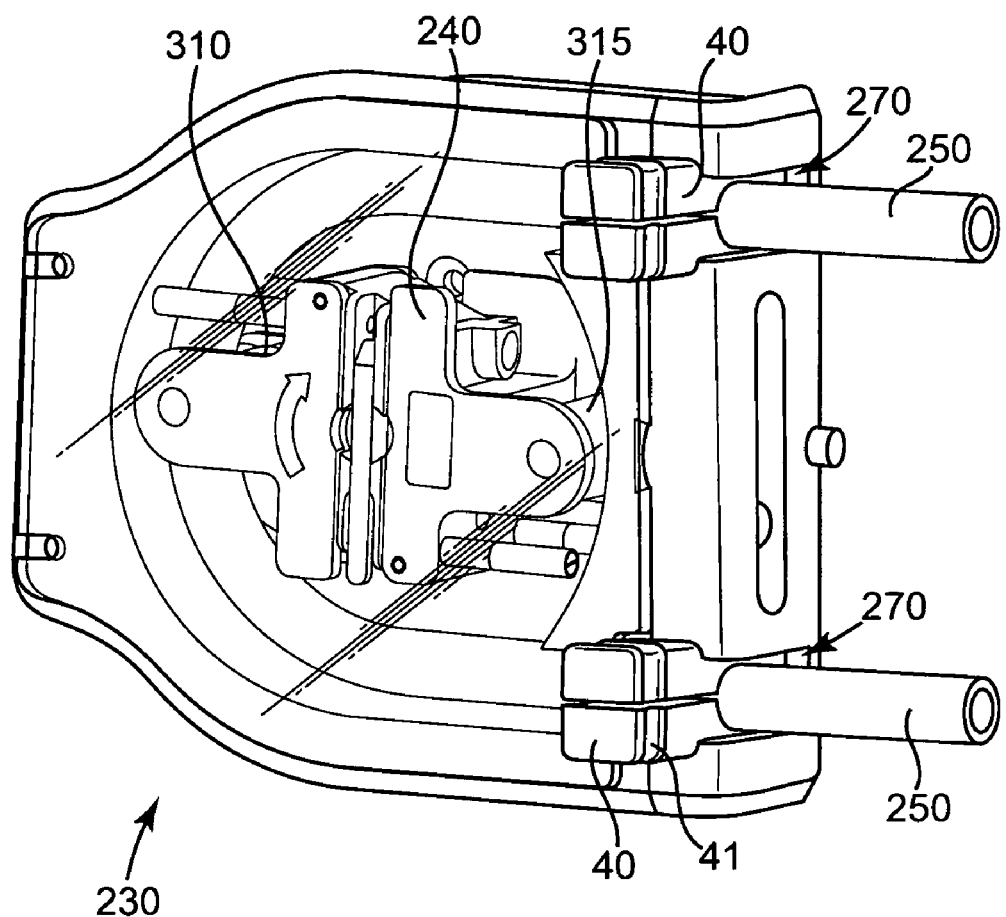
FIG. 1 is a perspective view of an exemplary embodiment of a pump head in accordance with the present invention.

As shown in FIG. 1, a pump head 230 of a roller pump comprises a pump stator 235 and a pump rotor 240. Pump stator 235 generally comprises a hollow chamber having a surface against which one or more hoses or tubing 250 are compressed by pump rotor 240. Pump rotor 240, which is rotatable about its longitudinal axis, is arranged in pump stator 235 in such a manner that pump rotor engages hoses 250 positioned in pump stator 235 with one or more rollers (preferably with two rollers, as shown in FIG. 1 by 310 and 315). On rotation of pump rotor 240, rollers 310 and 315 compress tubing 250 as they are rolled along tubing 250. A fluid medium contained in tubing 250 is then transported in a direction of pump rotor 240 rotation. In order to avoid tubing 250 from wandering within pump stator 235 while under the influence of rollers 310 and 315, one or more ends of tubing 250 entering and exiting pump stator 235 are fastened in place, or fixedly positioned, relative to pump stator 235.

FIG. 1 shows two tubing holding devices 40 in pump stator 235 by which tubing 250 is held at locations where the tubing 250 enters and exits the pump head 230. The purpose of tubing holding devices 40 is to hold tubing 250 in place relative to pump stator 235 so that tubing 250 is not displaced by the action of rollers 310 and 315 of pump rotor 240. Tubing holding device 40 comprises a clamping mechanism that, when in a closed position around a portion of tubing, uses positive, circumferential pressure and friction to securely hold, or fixedly capture, the tubing 250 in place relative to pump stator 235. The tubing holding devices 40 are preferably positioned at the entrance and exit points of the pump stator 235, but could alternatively be spaced inward. The tubing holding devices 40, of which there may alternatively be only one or a plurality, may be located anywhere that they are able to function to hold tubing and also do not interfere with the functionality of the rollers of the pump rotor 240.

A tubing holding device 40 is completely disengageable (i.e., removable or detachable) from pump head 230. The purpose of tubing holding device 40 being disengageable from pump head 230 is to allow interchangeably any number of different tubing holding devices 40 to be used in pump head 230. For example, a set of tubing holding devices 40 for a particular size or type of tubing may be completely removed from pump head 230 and replaced with another set of tubing holding devices 40 for a different size or type of tubing.

Tubing 250 that may be routed in pump head 230 is available in various types and sizes. The tubing 250 that is generally used in pump head 230, shown in FIG. 1, is polyvinyl chloride (PVC) tubing. However, the present invention contemplates using tubing of any suitable material that is either known or that may be developed in the future. The preferred sizes of tubing that are used in pump head 230 are ⅜ inch, ¼ inch and ⅛ inch tubing. However, the present invention contemplates using other sizes of tubing as well.

Figure 2:
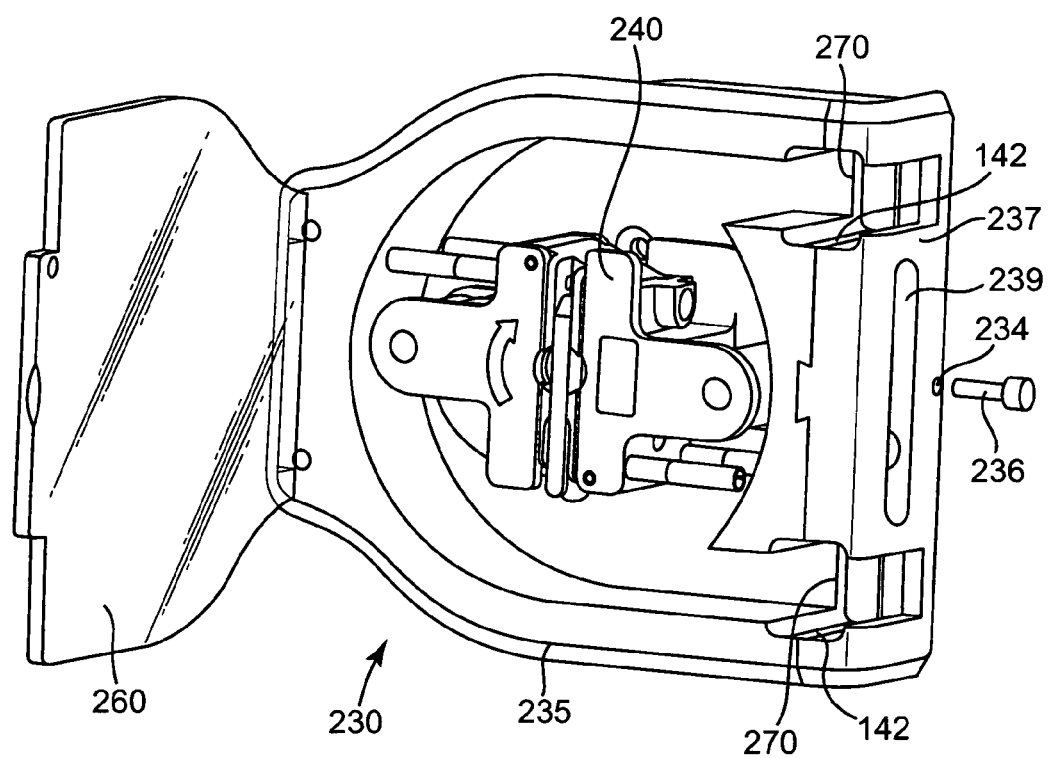
FIG. 2 is a perspective view of the pump head of FIG. 1 shown with cover open and a screw or attachment means removed from a front plate.

FIGS. 2-7 demonstrate a loading process for tubing holding devices 40 into pump head 230. FIG. 2 shows pump head 230 without tubing holding devices inserted. FIG. 2 also demonstrates the first step in loading tubing holding devices 40 into pump head 230, which is the removal of a screw 236 or other similar attachment means that holds a front plate 237 on pump stator 235. Preferably, pump stator 235 and front plate 237 together form a rigid walled cavity 270 to house each tubing holding device that may be inserted into pump head 230. Rigid walled cavity 270 is preferably shaped and sized to appropriately fit tubing holding device 40 such that the cavity 270 will hold tubing holding device 40 in place so as to fixedly capture tubing. Additionally, rigid walled cavity 270 is preferably configured such that in order to insert or remove a tubing holding device 40 from the cavity 270, front plate 237 is removed.

In FIG. 2, cover 260 is shown in an open position, so as to allow for loading of tubing holding devices 40 and tubing. A finger grip 239 is also shown, which is preferably cut into front plate 237 and can serve to assist in gripping front plate 237 for removal of front plate 237 from pump stator 235.

Figure 3:
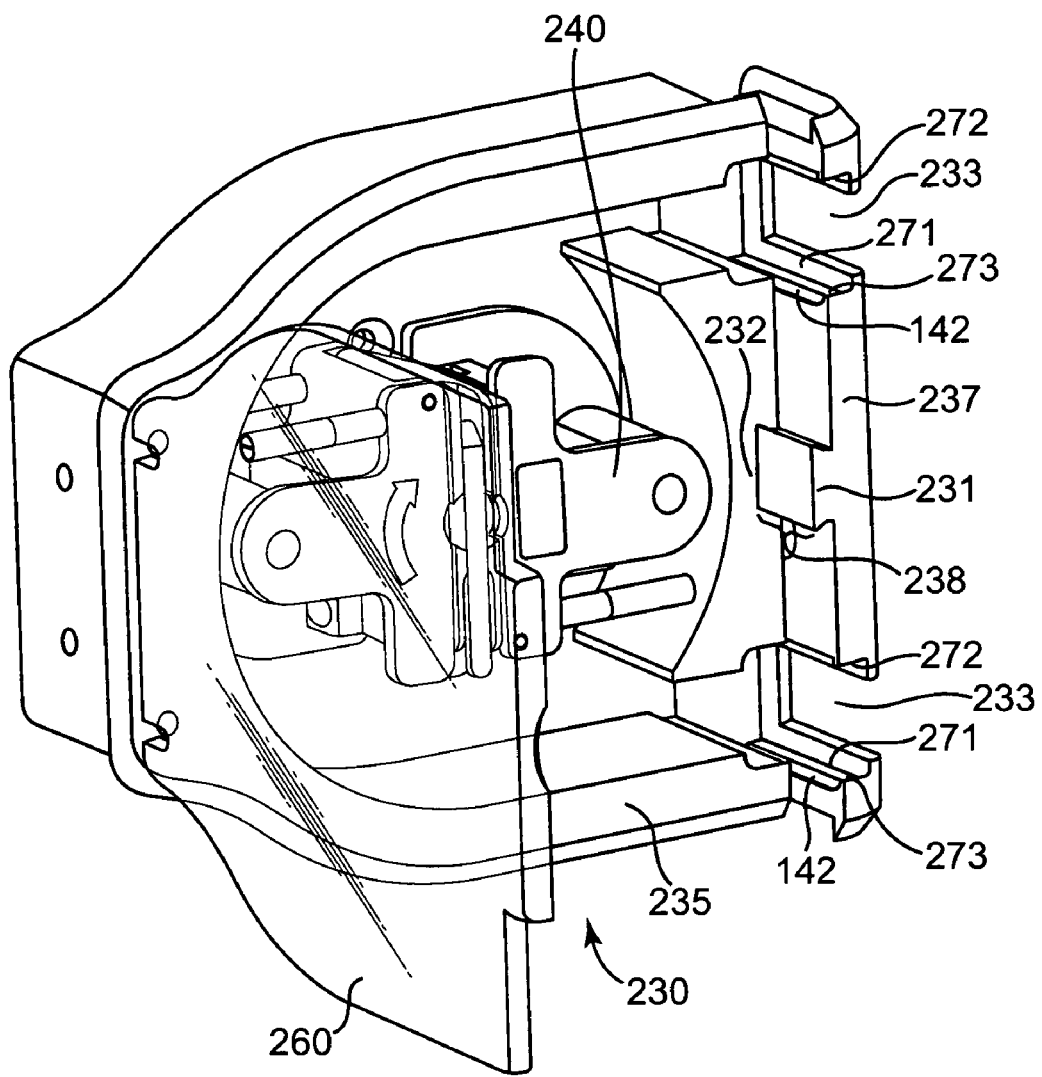
FIG. 3 is a perspective view of the pump head of FIG. 2 shown with the front plate partially removed from a pump stator.

FIG. 3 shows front plate 237 partially removed from pump stator 235. Front plate 237 is removed by sliding front plate 237 and pump stator 235 relative to one another, with the front plate 237 being slid outward towards the front of the pump head 230. As shown, a dovetail coupling mechanism 238 is used to attach front plate 237 and pump stator 235 together. The male portion 231 of the dovetail coupling 238 is shown included on the front plate 237, whereas the female portion 232 is shown on the pump stator 235. Alternatively, a male portion could be included on the pump stator 23 and a female portion on the front plate 237. Although a dovetail coupling mechanism is shown to removably attach the front plate 237 and pump stator 235, other similar attachment means are also contemplated by the present invention.

Figure 4:
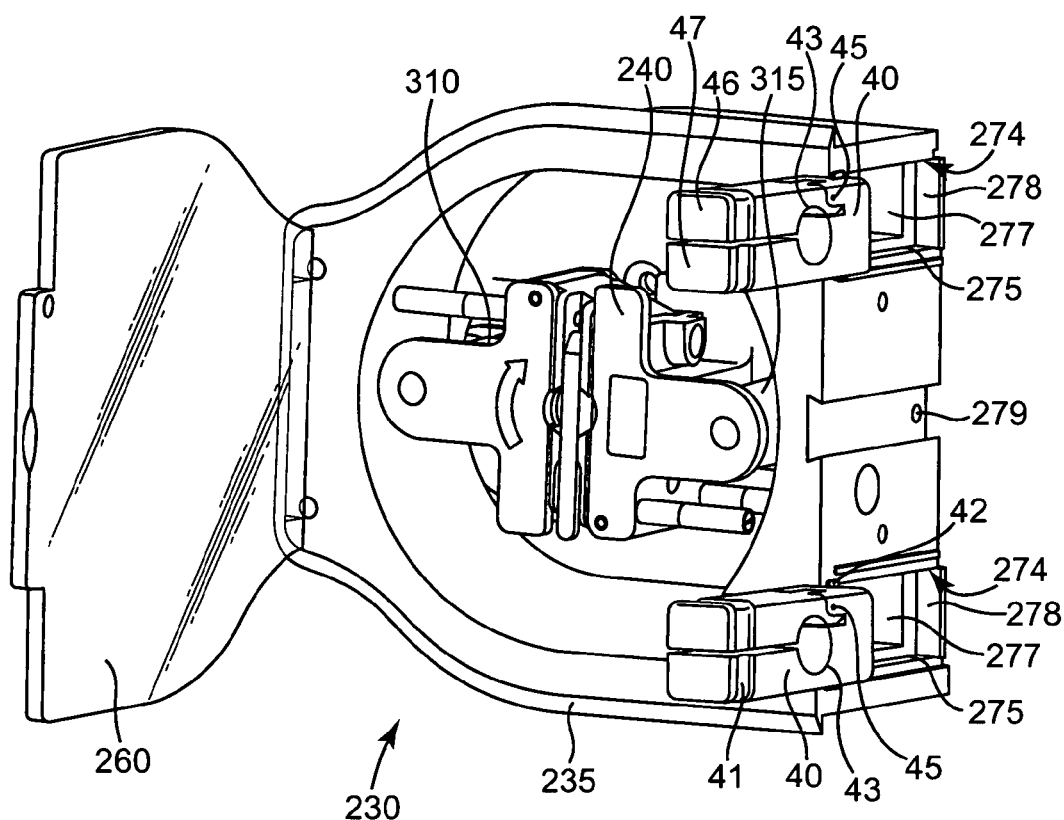
FIG. 4 is a perspective view of the pump head of FIG. 3 shown without the front plate portion and with two tubing holding devices shown placed in a portion of rigid walled cavities comprising portions of the pump stator.

As shown in FIGS. 2 and 3, rigid walled cavity 270 preferably comprises portions of both pump stator 235 and front plate 237. A front wall 271 of each rigid walled cavity 270 comprises a portion of the front plate 237. The front wall 271 also preferably includes a slot 233 through which tubing 250 will run after tubing 250 is loaded in tubing holding device 40 and tubing holding device 40 is fully engaged in rigid walled cavity 270. The size and the shape of slot 233 is preferably configured to accommodate one or more pieces of tubing loaded into pump head 230. The preferred shape of slot 233 shown in FIG. 3 is rectangular, although an elongated u-shape is also contemplated, for example. The rigid walled cavity 270 preferably further comprises side walls, with a portion of each side wall comprising a portion of both the front plate 237 and the pump stator 235. The portions of the first and second side walls of the rigid walled cavity 270 that comprise portions of the front plate 237 are shown in FIG. 3 as 272 and 273, respectively. The portions of the first and second side walls of the rigid walled cavity 270 that comprise the pump stator 235 are shown in FIG. 4 as 274 and 275, respectively. The back wall 276 of each rigid walled cavity 270, shown in FIG. 4, comprises a portion of the pump stator 235. As with the front wall 271, the back wall 276 of the rigid walled cavity 270 preferably includes a slot 277 to accommodate tubing passing through the cavity 270 once tubing holding device 40 is fully engaged in cavity 270. Preferably, slot 277 is rectangular in shape, but other shapes are also contemplated by the present invention. The bottom 278 of the rigid walled cavity 270 comprises a portion of the pump stator 235. The bottom 278 of the cavity 270 functions as a stop for tubing holding device 40 once fully inserted or engaged in cavity 270. Front plate 237 does not define any portion of the bottom since the front plate 237 is attached to the pump stator 235 after the tubing holding devices 40 are in place (as seen in FIG. 5).

FIG. 4 also shows two tubing holding devices 40 placed in the pump stator 235 adjacent the back walls 276 and portions of the side walls 274 and 275 of the rigid walled cavities 270. Front plate 237 is not shown in FIG. 4 because it can be detached when tubing holding devices 40 are placed as in the figure. During the tubing holding device 40 loading process, once the front plate 237 is removed or detached as in FIG. 4, tubing holding devices 40 can be placed in the portion of the rigid walled cavity 270 made up by the pump stator 235.

Figure 5:
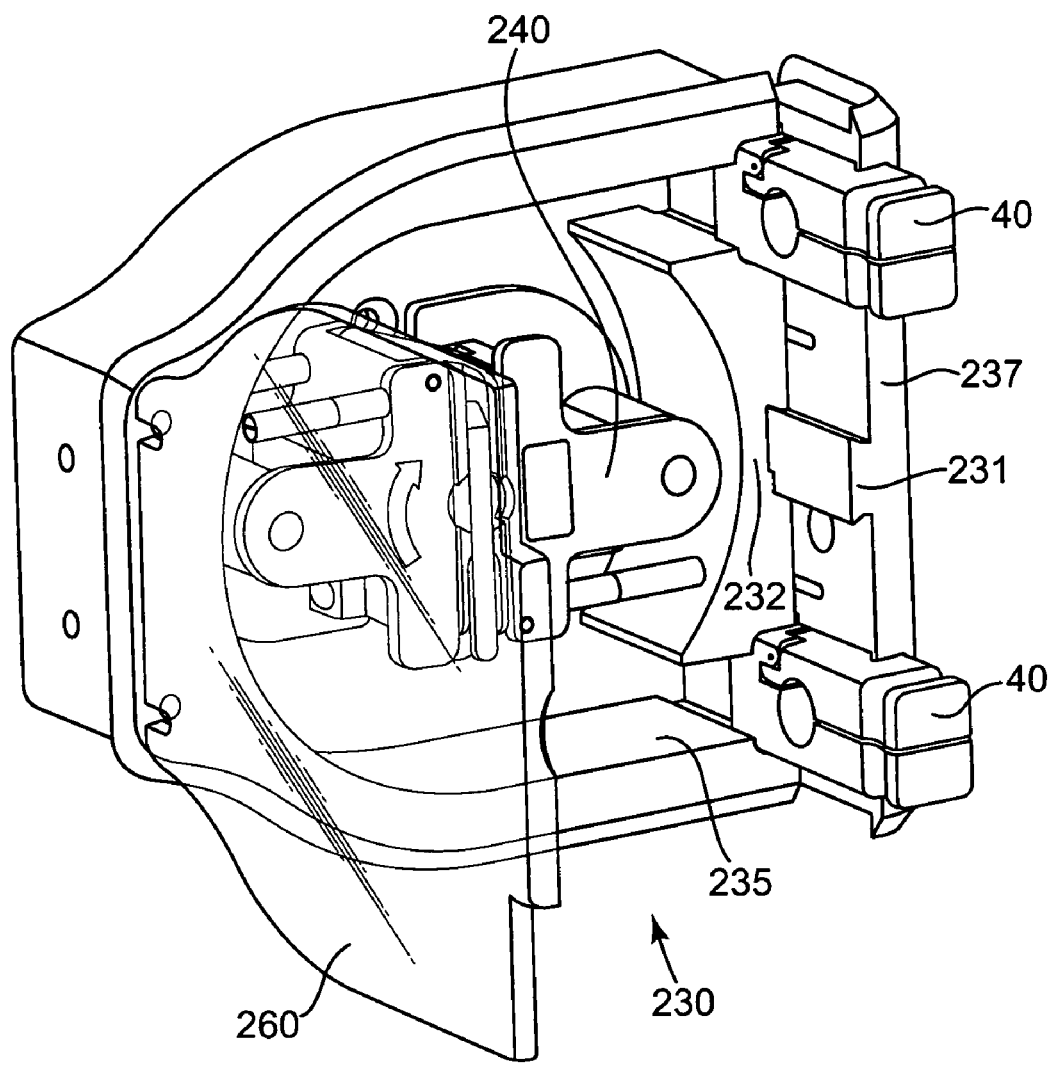
FIG. 5 is perspective view of the pump head of FIG. 4 shown with the front plate being slid over the two tubing holding devices and onto the pump stator.

FIG. 5 shows the next step in loading tubing holding devices 40, which is the front plate 237 being reattached to pump stator 235. Front plate 237 is preferably reattached by sliding the plate 237 after the tubing holding devices 40 are in place and by sliding the male portion 231 of the dovetail coupling mechanism 238 into the female portion 232 on the pump stator 235. Although not shown in the figure, front plate 237 is slid down to a position where a screw hole 234 (shown in FIG. 1) on front plate 237 lines up with a screw hole 279 (shown in FIG. 4) on pump stator 235. Screw 236 is then screwed into holes 234 and 279 to attach front plate 237 to pump stator 235.

By attaching front plate 237 to pump stator 235, tubing holding devices 40 may preferably not be completely removable or disengageable from rigid walled cavities 270. A preferred means for retaining tubing holding devices 40 in the rigid walled cavities 270 is formed by both the pump stator 235 and the front plate 237 includes the use of tabs 42 (shown in FIG. 4) on the tubing holding devices 40. Tabs 42 slidably fit in slots 142 (seen in FIG. 2) on each side of rigid walled cavity 270, after the front plate 237 is reattached. The slots 142 are preferably formed upon attachment of front plate 237 to pump stator 235 by space that is provided between the side walls 272 and 273 of the front plate 237 and the side walls 274 and 275 of the pump stator 235. The slots 142 are sized to allow the tabs 42 to slidably fit in the slots, and the slots 142 have a stop at the top that comprises a portion of the front plate 237 that extends over the top of the slots 142. The stop at the top of each slot 142 keeps tubing holding device 40 from being removed from pump stator 235 after tubing holding devices 40 are loaded and front plate 237 is attached to pump stator 235, but permits sliding of tubing holding devices 40 within the range of the slots 142.

The configuration of the rigid walled cavity 270 described above is the preferred embodiment. Other configurations of the rigid walled cavity 270 are, however, also contemplated by the present invention. The holding devices 40 and cavity 270 are preferably sized and shaped similarly to allow at least a range of sliding movement that may be limited by stops or not at all.

Figure 6:
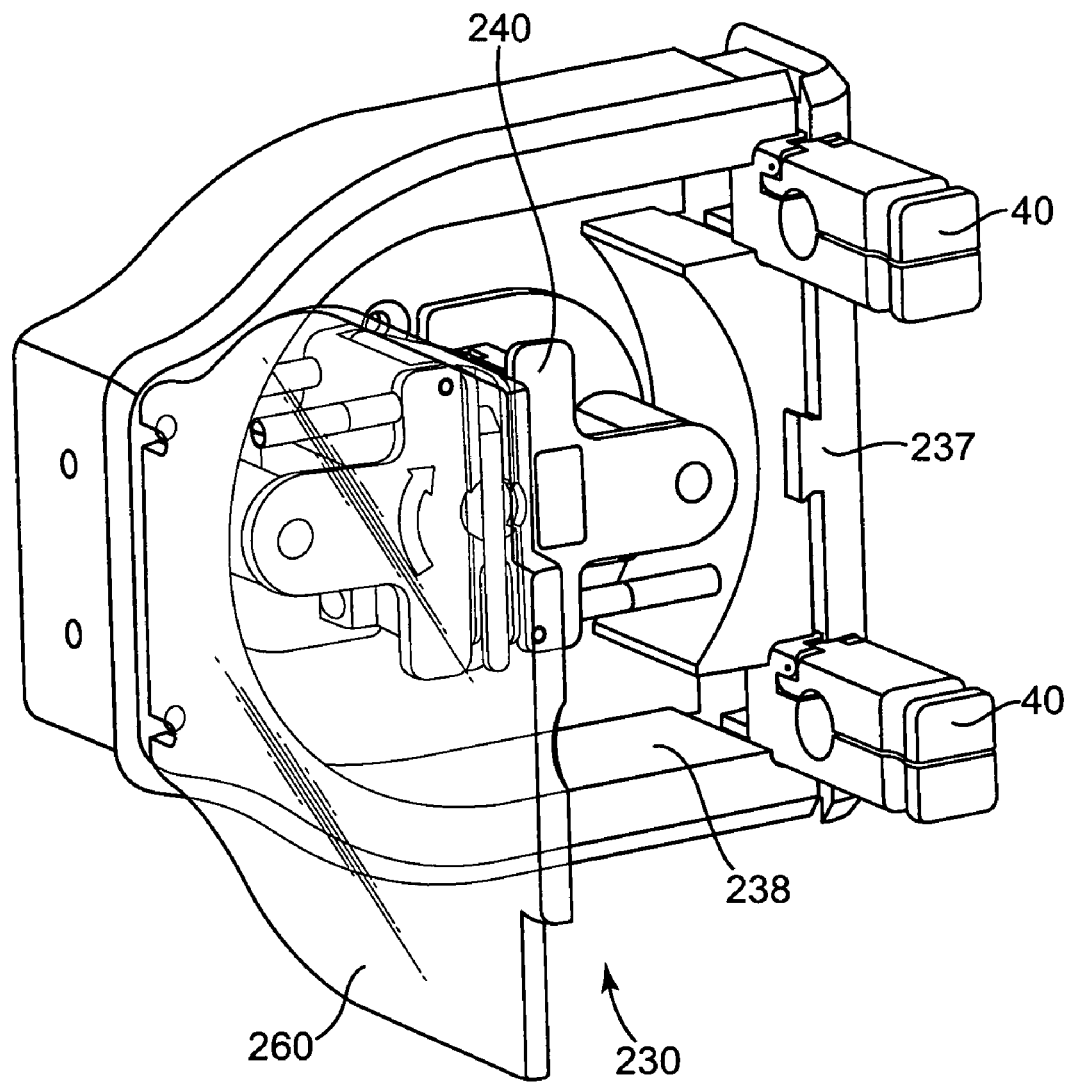
FIG. 6 is perspective view of the pump head of FIG. 5 shown with the front plate reattached to the pump stator, and with two tubing holding devices in the rigid walled cavities.
Figure 7:
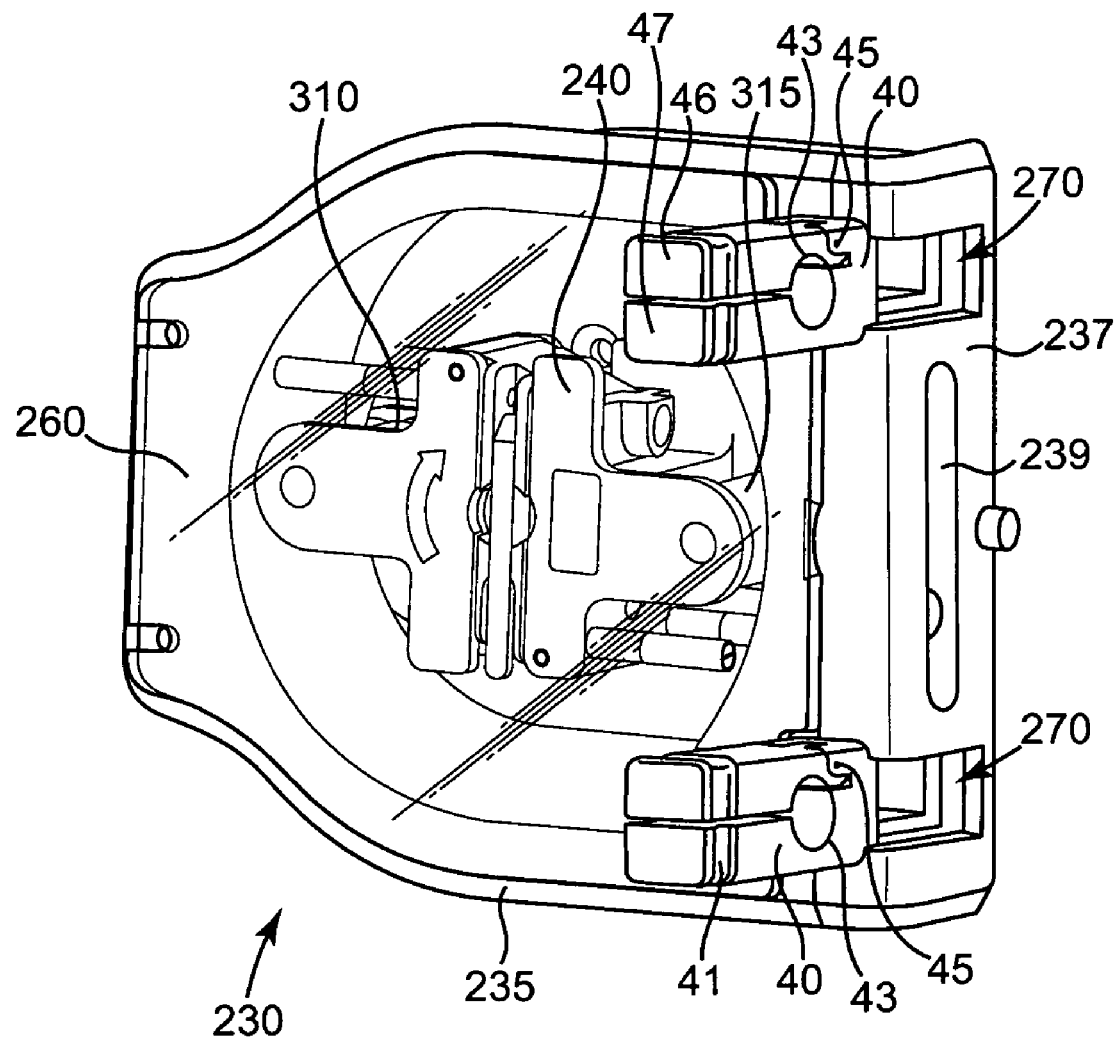
FIG. 7 is a perspective view of the pump head of FIG. 6 shown with a cover in a closed position.

FIG. 6 shows front plate 237 attached to pump stator 235 and tubing holding devices 40 loaded in pump head 230. Tubing holding devices 40 are shown in a partially engaged position, meaning that the tubing holding devices 40 are loaded in the rigid walled cavities 270 and retained by attachment of front plate 237, but are not slid down to a fully engaged position. The partially engaged position also allows the tubing holding device 40 to be opened and closed for loading and removing of tubing. A fully engaged position is when a tubing holding device 40 preferably contacts the bottom 278 of a rigid walled cavity 270 so that any tubing held by tubing holding devices 40 can be properly placed relative to pump stator 235 and pump rotor 240. The fully engaged position also preferably means that the tubing holding device will not be able to be opened for loading or removing of tubing. The next step in loading tubing holding devices 40 is shown in FIG. 7, which is to move the cover 260 to a closed position.

Figure 8:
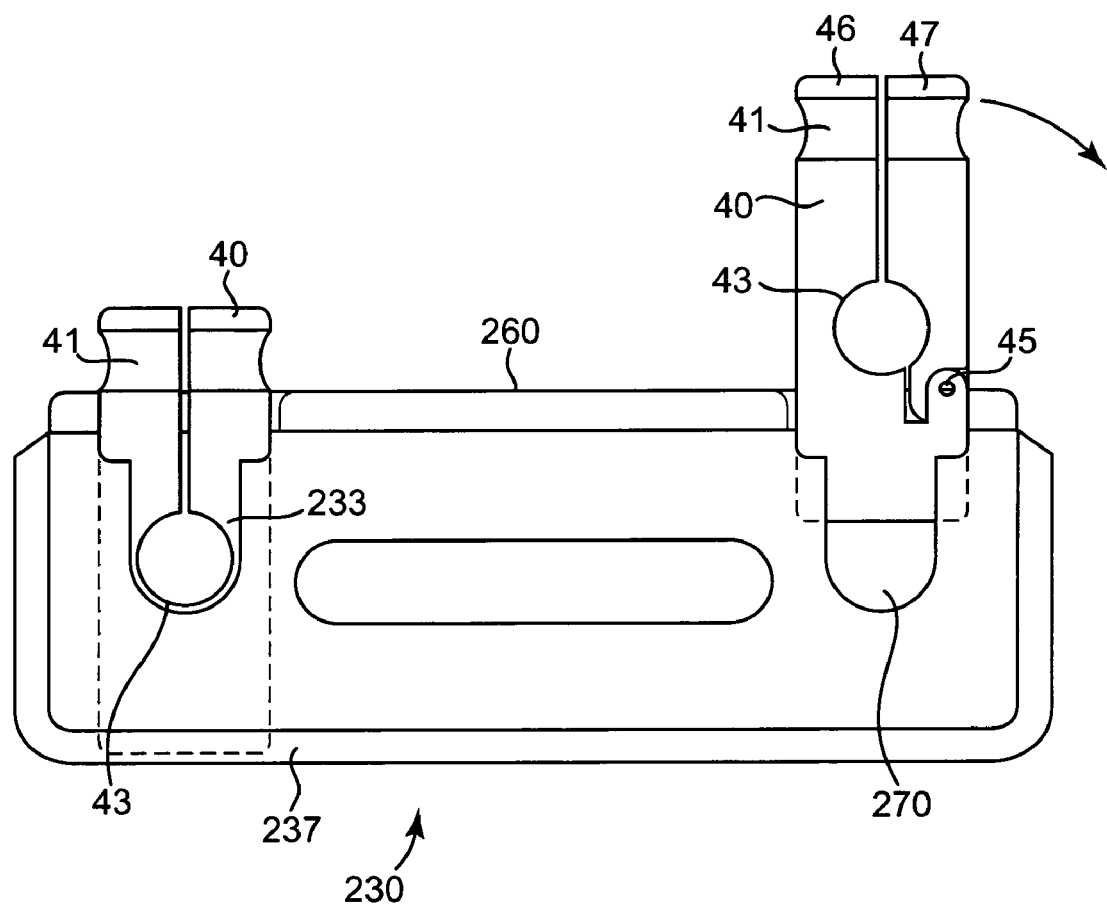
FIG. 8 is a side view of an exemplary embodiment of a pump head in accordance with the present invention shown from the front plate end with one tubing holding device being fully engaged in a rigid walled cavity and the other tubing holding device being partially engaged in a rigid walled cavity.

In FIGS. 4-7, tubing holding devices 40 are shown in a partially engaged position. FIG. 8 shows a side view of pump head 230 from the front plate 237 end. In the figure, one of the two tubing holding devices 40 (on left in figure) is shown fully engaged (i.e. fully inserted in rigid walled cavity 270 such that the tubing holding device 40 contacts the bottom 278 of rigid walled cavity 270) while the second tubing holding device 40 (on right) is shown partially engaged (i.e. loaded in the rigid walled cavities 270 and retained by attachment of front plate 237 so that tubing may be loaded or removed from device, but not moved down to a fully engaged position). In order to move between the fully engaged position and the partially engaged position, tubing holding device 40 is slid (up and down in FIG. 8) within the rigid walled cavity 270. Referring back to FIG. 1, tubing holding devices 40 are both shown in fully engaged positions while fixedly capturing portions of tubing 250.

A tubing holding device 40 of the present invention is preferably designed to be manually slid up and down in a rigid walled cavity 270 in a pump head 230 easily without tubing 250 loaded in the lumen 43 (finger grips for gripping tubing holding device are shown, for example, in FIG. 1 as 41). The lumen 43 of the tubing holding device 40 is preferably sized smaller than the tubing size that it is designed to hold (e.g., a lumen designed to hold ⅛ inch tubing is sized slightly less than ⅛ inch). Therefore, once tubing 250 is loaded in the tubing holding device 40 in the partially engaged position the larger tubing size tends to urge the holding device 40 to expand, which creates increased frictional contact with the rigid walled cavity 270. Then as the device 40 is slid to the fully engaged position in the rigid walled cavity 270, the device 40 exerts lateral forces on the walls of the rigid walled cavity 270 with such forces being transferred back to the device 40, in turn causing the device 40 to exert positive, circumferential force on the tubing 250. The positive, circumferential force on the tubing 250 preferably keeps the tubing 250 in place.

Tubing holding device 40 preferably comprises a material that is firm enough to allow the device 40 to fixedly capture tubing 250, while being lubricious enough to slide within rigid walled cavity 270 without damaging (e.g., gulling) the rigid walled cavity 270, which preferably comprises aluminum. One preferred material comprising tubing holding device 40 is Delrin® acetal resin (commercially available from E.I. DuPont de Nemours and Company, located in Wilmington, Del., U.S.A.). Some other exemplary materials that may comprise tubing holding device 40 include, but are not limited to, metals and other plastics (e.g., nylon).

FIG. 8 shows a partial side view of an exemplary tubing holding device 40 of the present invention. Tubing holding device 40 (shown on right in figure) is partially engaged in rigid walled cavity 270. A full perspective view of tubing holding device 40 can be seen by referring back to FIG. 4. The exemplary embodiment of the tubing holding device 40 of the present invention, as shown in FIGS. 4 and 8, comprises a first arm 47 and a second arm 46, wherein each arm defines a portion of a lumen 43. At least one arm (first arm 47 in figure) is moveable relative to the other arm (second arm 46 in figure) to permit access to the formed lumen 43. FIGS. 4 and 8 also show a preferred method of enabling the arms 46 and 47 to be moveable relative to one another, which is by connecting the arms 46 and 47 with a pivoting means, specifically a hinge 45. Other methods of enabling the arms to be moveable relative to one another are, however, also contemplated by the present invention. As can be seen in FIG. 8, first arm 47 may be pivoted in a direction as indicated by the arrow in the figure, thereby opening lumen 43 to an open position. In a closed position, first and second arms 46, 47 form the lumen 43. Lumen 43 may be used to fixedly capture a portion of tubing. The preferred configuration of the tubing holding device 40 including a hinge shown in FIGS. 4 and 8 allows for easy loading or removal of tubing into or out of lumen 43, while the tubing holding device 40 is in the partially engaged position. In the partially engaged position, at least one arm is moveable relative to the other arm to allow access to the lumen. However in the fully engaged position, it is preferred that neither arm 46 or 47 be moveable relative to the other arm so as to maintain the lumen 43 as formed. The walls of cavity 270 preferably prevent arms 46 and 47 from moving.

First and second arms 46, 47 of tubing holding device 40 are preferably sized and shaped and have an outer surface that allows tubing holding device 40 to be slid in rigid walled cavity 270 of pump head 230 causing tubing holding device 40 to be maintained in a closed position when in rigid walled cavity 270. Such a configuration of the arms 46, 47, additionally or alternatively, allows tubing holding device 40 to be slid to the partially engaged position in rigid walled cavity 270, where lumen 43 may be opened.

In one preferred embodiment, an outer surface of lumen 43 may be proportioned between arms 46 and 47 so that an unequal portion of the outer surface of lumen 43 is associated with each arm 46 and 47. For example, as shown in FIG. 8, the outer surface of the lumen 43 associated with arm 46 is greater than the outer surface of the lumen 43 associated with arm 47. In an alternative embodiment, an equal portion of the outer surface of the lumen 43 is associated with each arm 46 and 47. Another way of describing an unequal division of the lumen between the two arms is that tubing makes contact with greater than 180 degrees of the circumference of the lumen made up by one arm and makes contact with less than 180 degrees of the circumference of the lumen made up by the other arm. The purpose for one arm (e.g., 46) having a greater portion of the outer surface of the lumen 43 being associated with that arm (e.g. 46) than with the other arm (e.g., 47) is to enable that portion of the lumen 43 associated with that arm (e.g., 46) to hold tubing 250 while it is being loaded in the pump head 230. Often the pump head is oriented vertically during loading, as in FIG. 1, for example. A greater portion of the outer surface of the lumen 43 contacting tubing placed in the open lumen from below the tubing can help maintain the tubing 250 in the open lumen until the tubing holding device 40 is closed around the tubing 250.

Also, in the exemplary embodiment shown in FIG. 8, a pivot axis or hinge 45 is positioned in a location to allow tubing to be easily loaded into lumen 43 of tubing holding device 40 while tubing holding device 40 is in the partially engaged position. Therefore, for some desired tubing changes, tubing holding device need only be moved to the partially engaged position to exchange tubing. FIG. 8 includes one example of how the hinge 45 may be configured in the tubing holding device 40, and other configurations are also contemplated by the present invention.

Hinge 45 may comprise any means for pivoting first arm 47 relative to second arm 46 that is currently developed or that may be developed in the future. For example, hinge 45 may comprise a mechanical hinge or a living hinge. Other hinges or pivoting means are, however, also contemplated by the present invention. It is also contemplated that the tubing holding device 40 may comprise an appropriate flexible material that can allow the arms of the device to move relative to one another enough, so that a pivoting means or hinge is not necessary in the device 40.

Figure 9:
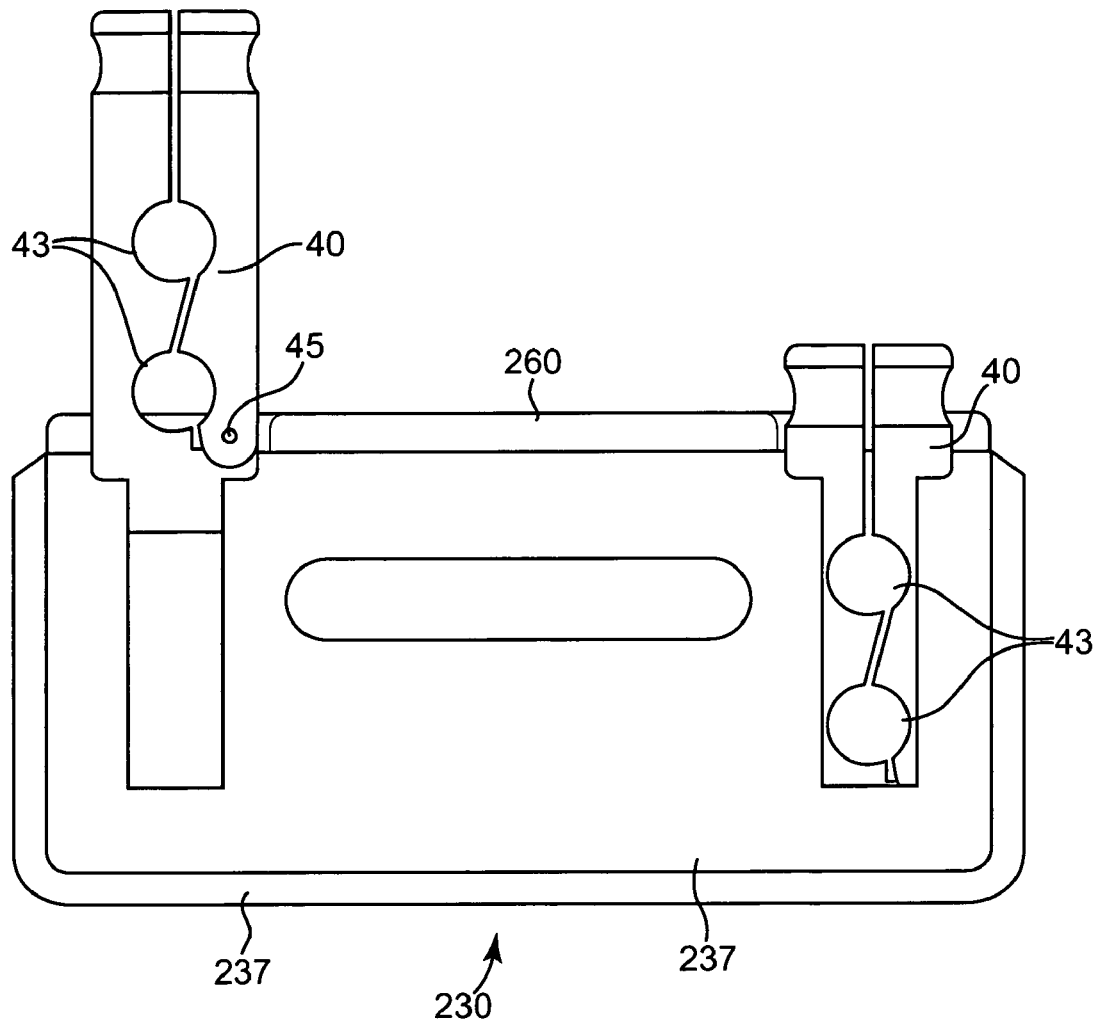
FIG. 9 is a side view of an exemplary embodiment of a pump head in accordance with the present invention shown from the front plate end with one tubing holding device being fully engaged in a rigid walled cavity and the other partially engaged in a rigid walled cavity and exposing plural tubing lumens.

FIG. 9 shows another exemplary embodiment of the present invention wherein tubing holding device 40 comprises more than one tubing lumen 43. The purpose of providing multiple lumens 43 is so that the tubing holding device 40 can hold in place one or more pieces of tubing at the same time. As shown in FIG. 9, tubing holding device 40 may comprise multiple lumens 43. Further, tubing holding device 40 may comprise multiple lumens 43 having different diameters.

Figure 10:
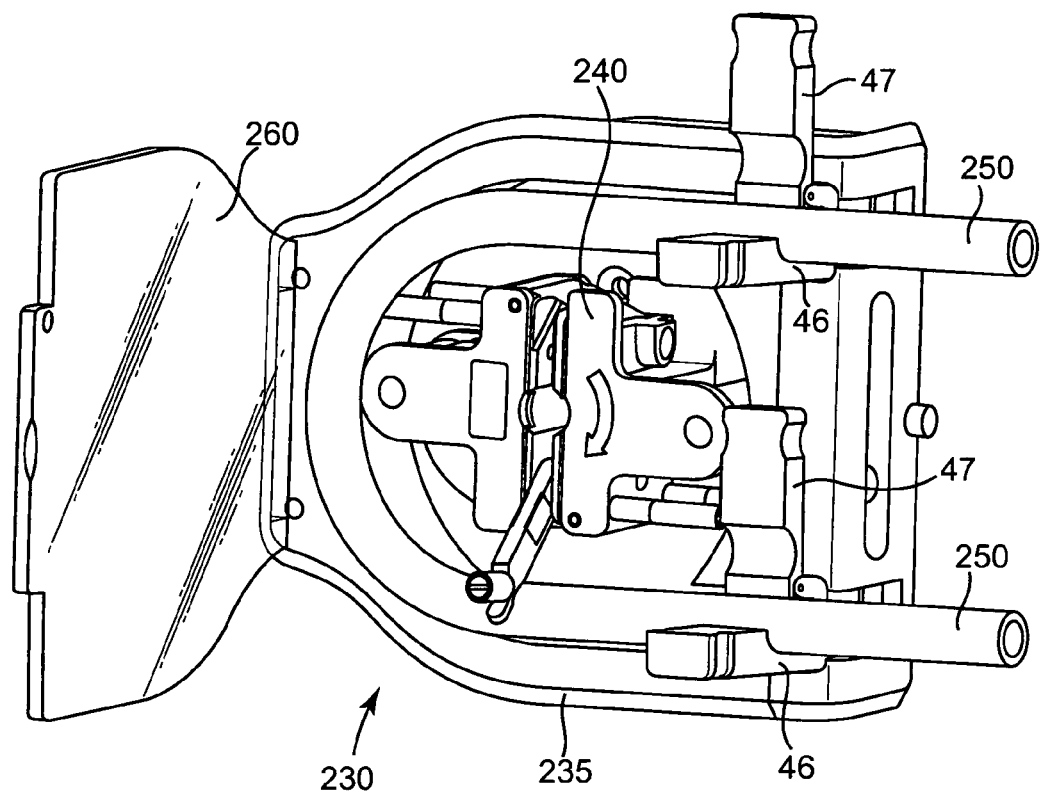
FIG. 10 is a perspective view of an exemplary embodiment of a pump head in accordance with the present invention shown with one arm of each first and second tubing holding devices being pivoted about first and second hinges, respectively, and with tubing inserted in lumen portions of tubing holding devices.

FIGS. 10 through 13, demonstrate a loading process for loading tubing 250 into pump head 230, according to an exemplary embodiment of the present invention. As shown in FIG. 10, cover 260 is in an open position, and first and second tubing holding devices 40 are partially engaged (i.e., slid outward). First arms 47 of both tubing holding devices 40 are pivoted relative to second arms 46, thereby opening first and second tubing lumens 43. A first portion of tubing 250 is then positioned within a portion of first lumen 43 (i.e., against the outer surface of lumen 43 associated with arm 46). A second portion of tubing 250 is then positioned within a portion of second lumen 43 (again i.e., against the outer surface of lumen 43 associated with arm 46). A third portion of tubing 250 is also positioned within pump stator 235.

Figure 11:
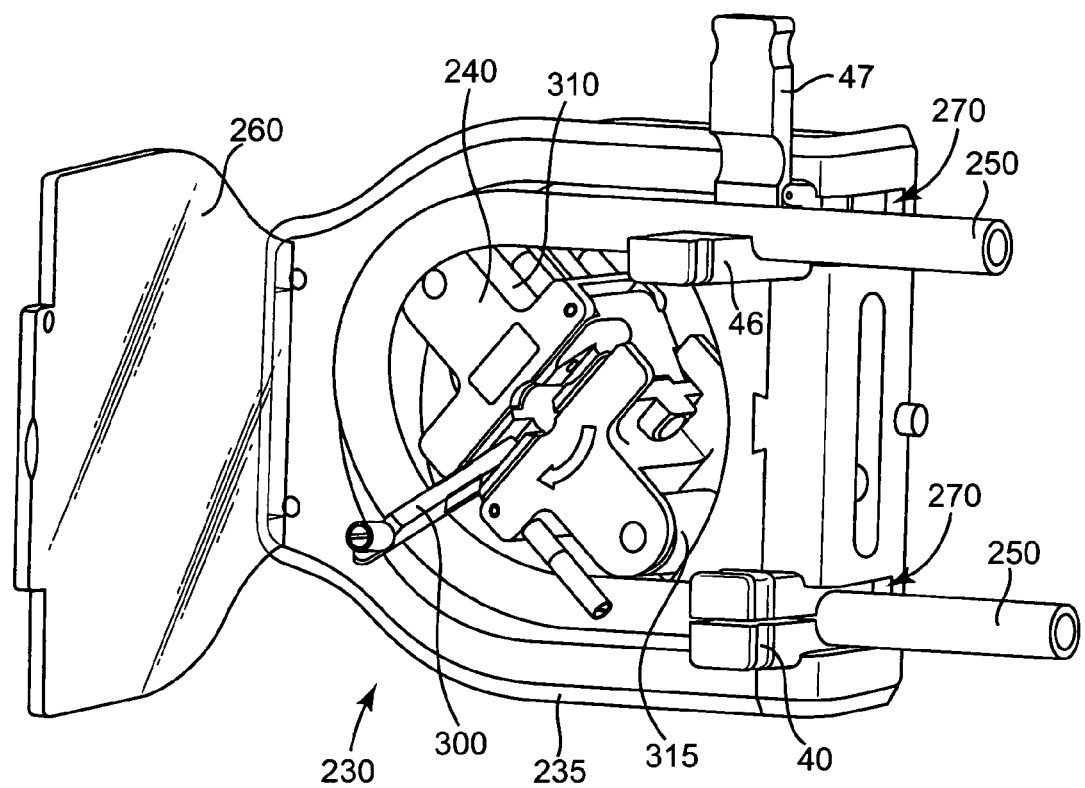
FIG. 11 is the pump head of FIG. 10 with one tubing holding device shown fixedly capturing tubing and in a fully engaged position and with the second holding device shown in a partially engaged and open position.

As shown in FIG. 11, the next step in the tubing loading process is to close the first tubing holding device 40 around tubing 250 and manually push tubing holding device 40 (with tubing) down into a first rigid walled cavity 270 until tubing holding device 40 preferably contacts the bottom 278 (seen in FIG. 4) of cavity 270 to retain arms 46 and 47 together and position tubing for use. Manual rotation mechanism or hand crank 300 is then preferably used to manually rotate or reposition pump rotor 240 so that the third portion of tubing 250 is correctly positioned within pump stator 235, thereby allowing pump rollers 310 and 315 of pump rotor 240 to properly engage tubing 250. Although the hand crank 300 is the preferred method for repositioning the pump rotor 240, automated mechanisms may also be used to reposition the pump stator 240 during the loading process.

Figure 12:
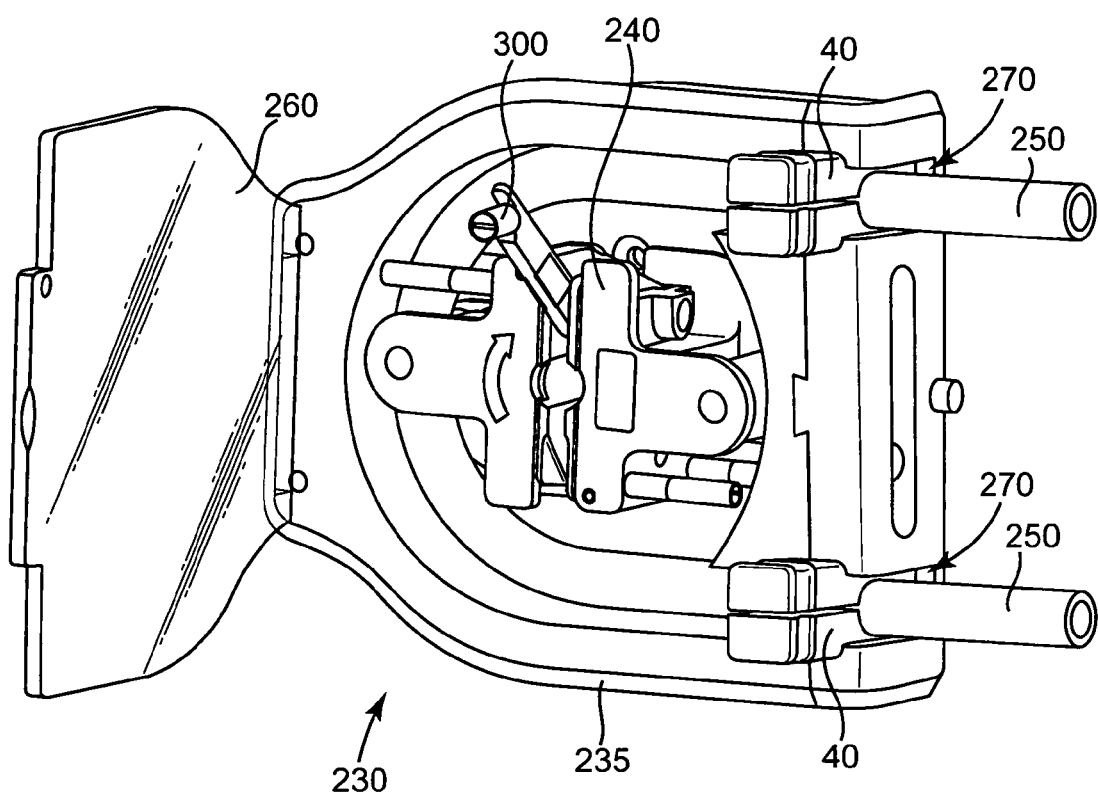
FIG. 12 is the pump head of FIG. 10 shown with both tubing holding devices fully engaged in the pump head and both fixedly capturing tubing.
Figure 13:
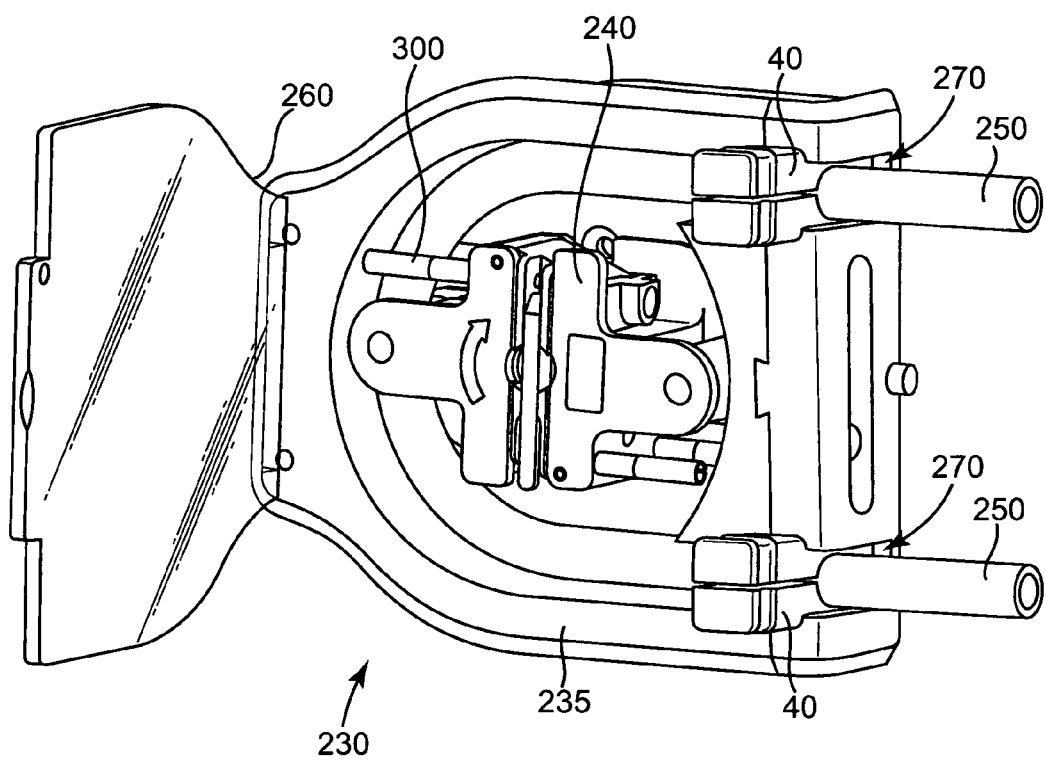
FIG. 13 is the pump head of FIG. 12 shown with a hand crank returned to a pump operating position.

As shown in FIG. 12, following correct positioning of tubing 250 within pump stator 235, the next step is to close second tubing holding device 40 around second portion of tubing 250 and manually push tubing holding device 40 (with tubing) down into a second rigid walled cavity 270 until tubing holding device 40 preferably contacts the bottom 278 (seen in FIG. 4) of cavity, thereby locking second portion of tubing 250 into position. As shown in FIG. 13, hand crank 300 can then be repositioned back into a pump operating position. Referring back to FIG. 1, the figure shows the result of the final step in the tubing loading process, which is that the cover 260 is closed.

Figure 14:
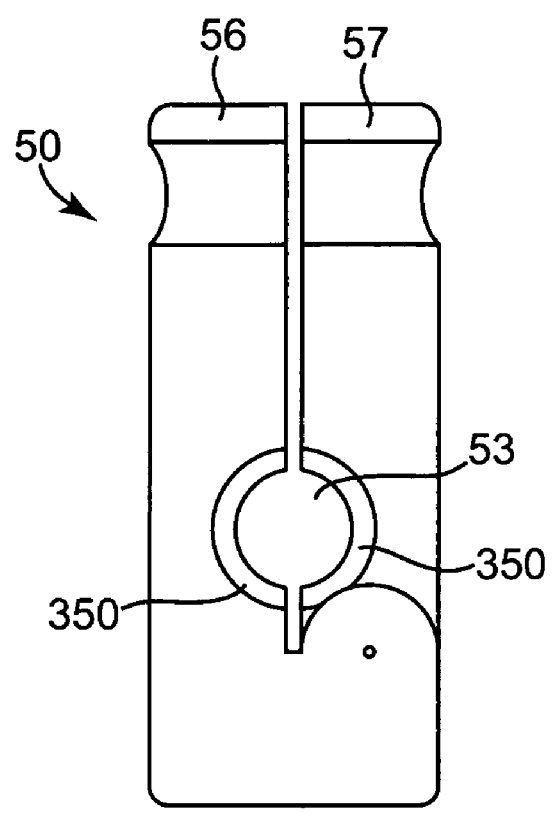
FIG. 14 is a side view of an exemplary embodiment of a tubing holding device in accordance with the present invention shown with shims included in the tubing lumen.
Figure 15:
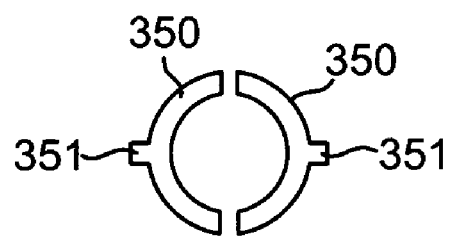
FIG. 15 is a side view of an exemplary embodiment of shims that may be used in an exemplary embodiment of a tubing holding device in accordance with the present invention.

In another exemplary embodiment of the present invention, as shown in FIGS. 14 and 15, lumen 53 of tubing holding device 50 may be adjustable in size so that tubing of various diameters may be used with the same tubing holding device 50. For example, as shown in FIG. 14, a pair of replaceable or interchangeable shims 350 may be used to adjust the size of lumen 53. The shims 350 may include one or more tabs 351, as shown in FIG. 15, which fit within corresponding slots in arms 56 and 57, in order to position the shims 350 in place in tubing holding device 50. Such tabs 351 and corresponding slots can be any shape that facilitates location of shims 350 in arms 46 and 47. Shims 350 can be any replaceable sizer with a lumen 53 shaped to receive tubing and that permits movement of the arms 56, 57 of the tubing loading device 50 for loading of tubing. There can be multiple sets of shims 350 provided for different tubing sizes.

Figure 16:
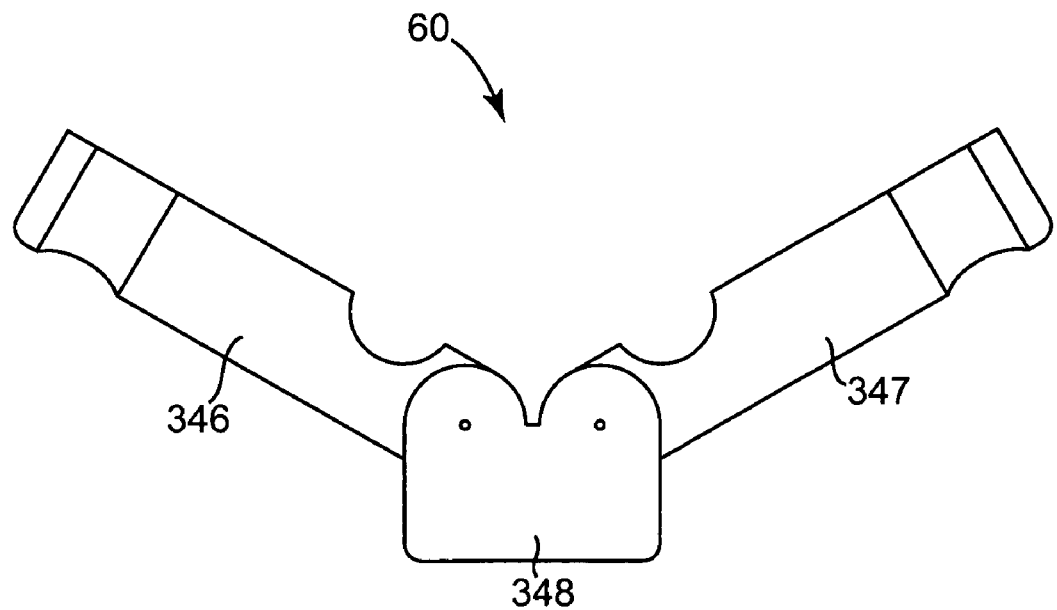
FIG. 16 is a side view of an exemplary embodiment of another tubing holding device in accordance with the present invention.

Various configurations of tubing holding devices are contemplated by the present invention. For example, as shown in FIG. 16, another embodiment of a tubing holding device 60 comprises a first member 346 having a proximal end and a distal end, a second member 347 having a proximal end and a distal end and a third member 348 having a proximal end and a distal end. In this embodiment, the proximal ends of the first and second members 346 and 347 are coupled with hinges 345 to the distal end of the third member 348. In a closed position, the first and second members 346 and 347 form a tubing lumen.

Figure 17:
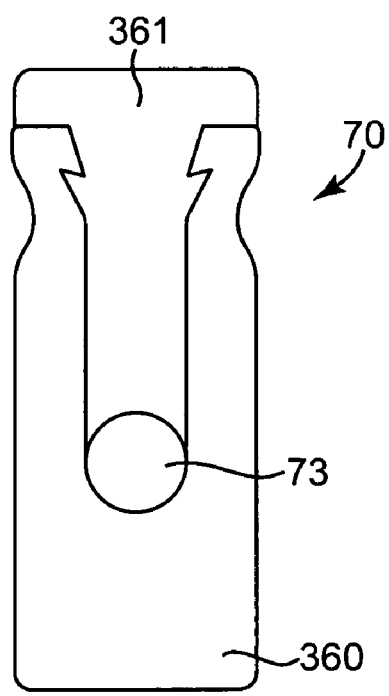
FIG. 17 is a side view of an exemplary embodiment of yet another tubing holding device in accordance with the present invention.

In another exemplary embodiment of the present invention, as shown in FIG. 17, a tubing holding device 70 comprises a first member 360 and a second member 361, wherein member 361 snap-fits into member 360 to form lumen 73. In this embodiment, in order to load tubing, the tubing is first positioned in member 360. Member 361 is then snap-fit around tubing, thereby forming lumen 73 and fixedly capturing tubing in device 70.

In an alternative embodiment of the present invention, not shown, a tubing holding device comprises a ratcheting mechanism or a locking pawl mechanism to clamp around tubing, thereby fixedly capturing tubing in the device in a plurality of different discrete positions to accommodate tubing of different sizes.

Pump head 230 including one or more tubing holding devices 40 in accordance with the present invention may be used or incorporated into any appropriate system or device in which blood or a similar fluid is desired to be driven or artificially circulated. An example of a system in which tubing holding device 40 can be included is disclosed in Italian Patent Application Nos. MO 2005A000244 (Borra et al., filed Sep. 23, 2005) and MO 2005A000243 (Borra et al., filed Sep. 23, 2005), which are incorporated by reference herein in their entirety.

Figure 18:
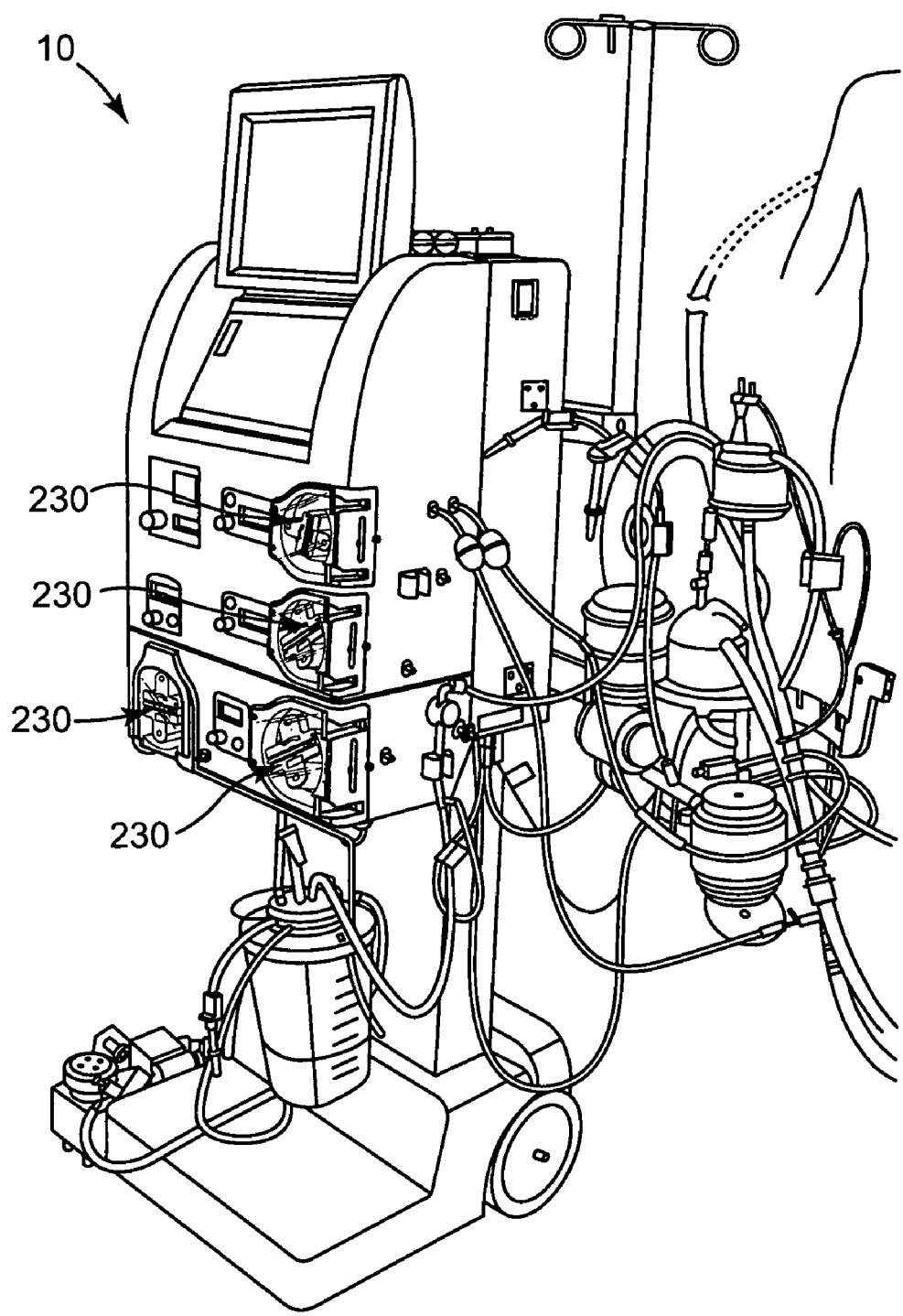
FIG. 18 is a perspective view of an advanced extracorporeal circulatory support system that incorporates exemplary embodiments of roller pump heads and tubing holding devices in accordance with the present invention.

One particular system in which pump head 230 and tubing holding device may be used is illustrated in FIG. 18, which is an advanced electromechanical extracorporeal circulatory support system 10 used, for example, during cardiopulmonary bypass procedures. As shown in FIG. 18, four roller pump heads 230, each including two tubing holding devices, are included in system 10. System 10, shown in FIG. 18, is similar to a CPB system commercially sold by Medtronic, Inc. (Minneapolis, Minn., U.S.A.), which is called the Performer-CPB System.

Although the present invention is described as possibly including tubing holding devices being incorporated into a CPB system as described above, the tubing holding devices of the present invention may be incorporated into any suitable system including roller pumps. More broadly, the tubing holding devices may be incorporated into any suitable system in which tubing is desired to be held in place, with such system not being limited to a system including the use of roller pumps.

All patents, patent applications and publications mentioned herein are incorporated by reference in their entirety. It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

The invention claimed is:

1. A tubing holding device used in a pump comprising a rigid walled cavity for slidably receiving the tubing holding device, the tubing holding device comprising:
    a first arm defining a first portion of a lumen for capturing tubing; and
    a second arm defining a second portion of the lumen for capturing tubing,
    wherein at least one of the first and second arms is moveable relative to the other arm to allow the lumen to be opened to load tubing into or remove tubing from the lumen while the tubing holding device is partially slidably received within the rigid wailed cavity, and closed to fixedly capture tubing in the lumen, and further wherein the first and second arms are sized and shaped and have an outer surface to allow the tubing holding device to be slid into the rigid walled cavity of the pump, with the first and second arms closed, causing the tubing holding device to be maintained in a closed position when fully within the rigid walled cavity of the pump, the tubing holding device also comprising a tab that is sized and shaped to slidably move along the rigid walled cavity in a slot and to engage a stop of the rigid walled cavity to prevent removal of the tubing holding device, thereby maintaining partial engagement in the rigid walled cavity.

2. The tubing holding device of claim 1, wherein the lumen comprises an outer surface, and the lumen outer surface of the first arm is greater than the lumen outer surface of the second arm.

3. The tubing holding device of claim 1, further comprising a means for pivoting at least one of the first and second arms relative to the other arm.

4. The tubing holding device of claim 1, wherein the lumen may be adjusted in size.

5. The tubing holding device of claim 1, further comprising at least one shim, wherein the at least one shim is positioned in the lumen to permit the lumen to fixedly capture tubing of a different size.

6. The tubing holding device of claim 1, wherein the first and second arms define portions of a plurality of lumens.

7. A tubing holding device used in a pump comprising a rigid walled cavity for slidably receiving the tubing holding device, the tubing holding device comprising:
    a first arm defining a first portion of a lumen for capturing tubing; and
    a second arm defining a second portion of the lumen for capturing tubing,
    wherein at least one of the first and second arms is moveable relative to the other atm to allow the lumen to be opened to load tubing into or remove tubing from the lumen and closed to fixedly capture tubing in the lumen, and wherein the lumen comprises an outer surface, and further wherein the tubing holding device includes an end surface for engagement with a bottom surface of the rigid walled cavity of a pump, and the first arm is pivotally connected with the second arm at a location spaced from the end surface so that a portion of the tubing holding device can be partially slidably received within the rigid walled cavity while also permitting pivotal movement of the first arm relative to the second arm so that tubing can be loaded into the tubing holding device.

8. The tubing holding device of claim 7, wherein the first and second arms are sized and shaped and have an outer surface to allow the tubing holding device to be slid into the rigid walled cavity of the pump causing the tubing holding device to be maintained in a closed position when in the rigid walled cavity of the pump.

9. The tubing holding device of claim 7, further comprising a means for pivoting at least one of the first and second arms relative to the other arm.

10. The tubing holding device of claim 7, wherein the lumen may be adjusted in size.

11. The tubing holding device of claim 7, further comprising at least one shim, wherein the at least one shim is positioned in the lumen to permit the lumen to fixedly capture tubing of a different size.

12. The tubing holding device of claim 7, wherein the first and second arms define portions of a plurality of lumens.

13. A roller pump for pumping fluids through a tubing, the roller pump comprising:
    a pump stator comprising a hollow chamber having a surface, and at least a portion of at least one rigid walled cavity;
    a pump rotor comprising at least one roller and having a longitudinal axis, wherein the pump rotor is arranged in the hollow chamber of the pump stator for rotation about its longitudinal axis, and when tubing is positioned in the roller pump, a first portion of the tubing is positioned against the surface of the pump stator, and during rotational movement of the pump rotor, the first portion of tubing is compressed against the surface of the pump stator by the at least one roller of the pump stator as the at least one roller travel along the first portion of tubing; and at least one tubing holding device that comprises a first arm and a second arm, wherein the first and second arms each define a portion of a lumen that is used to fixedly capture a second portion of tubing relative to the pump stator, wherein at least one of the first and second arms is moveable relative to the other arm to allow the lumen to be opened to load the second portion of tubing into or remove the second portion of tubing from the lumen while the tubing holding device is partially slidably received within the rigid walled cavity, or closed to fixedly capture the second portion of tubing in the lumen relative to the pump stator, and further wherein the tubing holding device is sized and shaped similar to the size and shape of the rigid walled cavity so as to be slidably disposed in the at least one rigid walled cavity and slidable between a loading position, in which the tubing holding device is partially slidably received within the rigid walled cavity with movement permitted between the first and second arms, and a fully engaged position, in which the first and second arms of the tubing holding device are maintained in a closed position.

14. The roller pump of claim 13, wherein the at least one tubing holding device is disengageable from the roller pump and may be exchanged with a different tubing holding device.

15. A method of loading a tubing in a roller pump, wherein the roller pump comprises a pump stator that comprises at least a portion of at least one rigid walled cavity slidably receiving a tubing holding device, a pump rotor; wherein said tubing holding device comprises a first arm and a second arm, wherein the first and second arms each define a portion of a lumen, at least one of the first and second arms is moveable relative to the other arm, the tubing holding device disposed in the at least one rigid walled cavity and being slidable along plural surfaces of the rigid walled cavity between a loading position and a fully engaged position, the method comprising the steps of:

positioning the at least one tubing holding device in a loading position with the tubing holding device partially engaged along plural surfaces the rigid walled cavity;

moving the first arm of the at least one tubing holding device relative to the second arm to open up the lumen;

placing a portion of the tubing in the open lumen of the at least one tubing holding device;

moving the first arm of the at least one tubing holding device relative to the second arm to close the lumen and fixedly capture the portion of tubing; and sliding the at least one tubing holding device further along the plural surfaces of the rigid walled cavity so as to maintain the first and second arms together with the closed lumen and thus fixedly position the portion of tubing relative to the pump stator.

16. The roller pump of claim 11, further comprising a front plate that is removably attached to the pump stator, wherein the at least one rigid walled cavity further comprises at least a portion of the front plate.

17. The method of claim 15, wherein the lumen comprises an outer surface, and the lumen outer surface of the second arm is greater than the lumen outer surface of the first arm, and the portion of tubing is placed in the portion of the lumen that is adjacent to the lumen outer surface of the second arm.

\* \* \* \* \*